United States Patent
Lang et al.

(10) Patent No.: US 10,941,103 B2
(45) Date of Patent: Mar. 9, 2021

(54) PROCESS FOR CONTINUOUSLY PREPARING N-BUTYL ACRYLATE OR ISOBUTYL ACRYLATE

(71) Applicant: BASF SE, Ludwigshafen am Rhein (DE)

(72) Inventors: Ortmund Lang, Ludwigshafen (DE); Tim Blaschke, Antwerp (BE); Christian Raith, Ludwigshafen (DE); Michael Schafranka, Ludwigshafen (DE); Claus Hechler, Ludwigshafen (DE)

(73) Assignee: BASF SE, Ludwigshafen am Rhein (DE)

( * ) Notice: Subject to any disclaimer, the term of this patent is extended or adjusted under 35 U.S.C. 154(b) by 0 days.

(21) Appl. No.: 16/636,703

(22) PCT Filed: Aug. 13, 2018

(86) PCT No.: PCT/EP2018/071863
§ 371 (c)(1),
(2) Date: Feb. 5, 2020

(87) PCT Pub. No.: WO2019/034577
PCT Pub. Date: Feb. 21, 2019

(65) Prior Publication Data
US 2020/0239400 A1      Jul. 30, 2020

(30) Foreign Application Priority Data
Aug. 17, 2017   (EP) .................................. 17186691

(51) Int. Cl.
*C07C 67/08*   (2006.01)
*C07C 67/54*   (2006.01)
(Continued)

(52) U.S. Cl.
CPC .............. *C07C 67/08* (2013.01); *C07C 67/54* (2013.01); *C07C 67/58* (2013.01); *C07C 69/54* (2013.01)

(58) Field of Classification Search
None
See application file for complete search history.

(56) References Cited

U.S. PATENT DOCUMENTS

| 4,280,010 A * | 7/1981 | Erpenbach | .............. C07C 67/08 |
|  |  |  | 560/205 |
| 6,482,976 B1 * | 11/2002 | Ho | .......................... C07C 67/08 |
|  |  |  | 560/205 |

(Continued)

FOREIGN PATENT DOCUMENTS

| DE | 196 04 267 A1 | 8/1997 |
| DE | 102 58 329 A1 | 7/2003 |

(Continued)

OTHER PUBLICATIONS https://pubchem.ncbi.nlm.nih.gov/compound/1-butanol#section=Density&fullscreen=true, downloaded on Jun. 18, 2020 (Year: 2020).*

(Continued)

*Primary Examiner* — Amy C Bonaparte
(74) *Attorney, Agent, or Firm* — Oblon, McClelland, Maier & Neustadt, L.L.P.

(57) ABSTRACT

A process for continuously preparing a butyl acrylate $H_2C=CH-C(=O)OR$, with R=n-butyl or isobutyl, wherein aqueous 3-hydroxypropionic acid is converted under dehydrating and esterifying conditions in the presence of the corresponding butanol R—OH in a reactor with a rectification column and butyl acrylate formed, unconverted butanol and water used and formed are distilled off overhead as a ternary azeotrope, after separation into a liquid aqueous phase and liquid organic phase each of the aqueous and (Continued)

organic phases is at least partly discharged, and the organic phase comprising the butyl acrylate and the butanol is subjected to distillative separation.

19 Claims, 2 Drawing Sheets

(51) Int. Cl.
  *C07C 67/58* (2006.01)
  *C07C 69/54* (2006.01)

(56) References Cited

U.S. PATENT DOCUMENTS

| | | |
|---|---|---|
| 2005/0221457 A1 | 10/2005 | Tsobanakis et al. |
| 2009/0298144 A1 | 12/2009 | Tsobanakis et al. |
| 2013/0150616 A1 | 6/2013 | Tsobanakis et al. |
| 2013/0245309 A1 | 9/2013 | Chalfant et al. |
| 2014/0364643 A1 | 12/2014 | Tsobanakis et al. |

FOREIGN PATENT DOCUMENTS

| | | |
|---|---|---|
| DE | 10 2005 053 982 A1 | 5/2006 |
| EP | 0 765 859 A1 | 4/1997 |
| EP | 1 182 189 B1 | 3/2005 |
| WO | WO 03/082795 A2 | 10/2003 |
| WO | WO 2012/071158 A1 | 5/2012 |
| WO | WO 2012/074818 A2 | 6/2012 |
| WO | WO 2015/036218 A1 | 3/2015 |

OTHER PUBLICATIONS

U.S. Appl. No. 16/062,359, filed Jun. 14, 2018, US 2019-0002389 A1, Horstmann, C., et al.
U.S. Appl. No. 16/472,018, filed Jun. 20, 2019, US 2020-0095185 A1, Lang, O., et al.
International Search Report dated Oct. 23, 2018 in PCT/EP2018/071863 filed on Aug. 13, 2018, citing documents AA-AE, AJ and AK therein, 2 pages.
Extended European Search Report dated Feb. 8, 2018 in European Patent Application No. 17186691.6 (with English translation of Category of Cited Documents, 4 pages).

\* cited by examiner

PROCESS FOR CONTINUOUSLY PREPARING N-BUTYL ACRYLATE OR ISOBUTYL ACRYLATE

The invention relates to a process for continuously preparing a butyl acrylate $H_2C=CH—C(=O)OR$, with R=n-butyl or isobutyl.

Processes for preparing alkyl acrylates from 3-hydroxypropionic acid are known. In principle, 3-hydroxypropionic acid can first be esterified with an alcohol in a first step and then the resulting 3-hydroxypropionic ester can be dehydrated to the corresponding alkyl acrylate in a subsequent step. Alternatively, 3-hydroxypropionic acid can also first be dehydrated in a first step and then the resulting acrylic acid can be esterified with an alcohol in a subsequent step.

WO 03/082795 A2 (Cargill, Inc.) describes, in example 13 (page 14), a one-pot synthesis of n-butyl acrylate proceeding from aqueous 3-hydroxypropionic acid and n-butanol (catalyst: $H_2SO_4$). The process is effected in three steps: firstly, the water is completely distilled off, then n-butanol is removed in a distillation apparatus and, finally, after lowering the temperature and pressure, the n-butyl acrylate product is distilled out of the residue. The yield is only 37%.

WO 2015/036218 A1 (BASF SE) describes a process for dehydrating aqueous 3-hydroxypropionic acid to acrylic acid.

The esterification of acrylic acid with an alcohol can especially be effected by the processes according to DE 196 04 267 A1 (BASF AG) or EP 765 859 A1 (BASF AG): DE 196 04 267 A1 discloses a process for continuously preparing alkyl esters of (meth)acrylic acid, wherein the workup is effected in two connected rectification units. EP 765 859 A1 teaches a process for continuously preparing alkyl acrylates in which the reaction zone consists of a cascade of at least two series-connected reaction regions.

EP 1 182 189 B1 (Rohm and Haas Company) relates to a process for continuously recovering n-butyl acrylate from an esterification reaction mixture.

WO 2012/071158 A1 (Rohm and Haas Company) describes a specific distillation process for $C_{1-4}$-alkyl (meth) acrylates, wherein the evaporated reactor contents are guided directly into a column.

One possible route for preparation of 3-hydroxypropionic acid proceeds via glucose through fermentation, wherein the glucose is obtained from renewable raw materials, for example corn. The preparation of 3-hydroxypropionic acid by fermentation is described, for example, in WO 2012/074818 A2 (Novozymes, Inc.).

It was an object of the present invention, overcoming disadvantages of the prior art, to provide an improved economically viable process for preparing n-butyl acrylate and isobutyl acrylate. The preparation process should additionally be particularly simple to implement and conduct, and should additionally be particularly economically viable.

Accordingly, a process for continuously preparing an alkyl acrylate $H_2C=CH—C(=O)OR$, with R=n-butyl or isobutyl, has been found, which comprises converting aqueous 3-hydroxypropionic acid under dehydrating and esterifying conditions in the presence of the corresponding butanol R—OH in a reactor with a rectification column and distilling off butyl acrylate formed, unconverted butanol and water used and formed overhead as a ternary azeotrope, after separation into a liquid aqueous phase and liquid organic phase at least partly discharging each of the aqueous and organic phases, and distillatively separating the organic phase comprising the butyl acrylate and the butanol.

Figure 1:
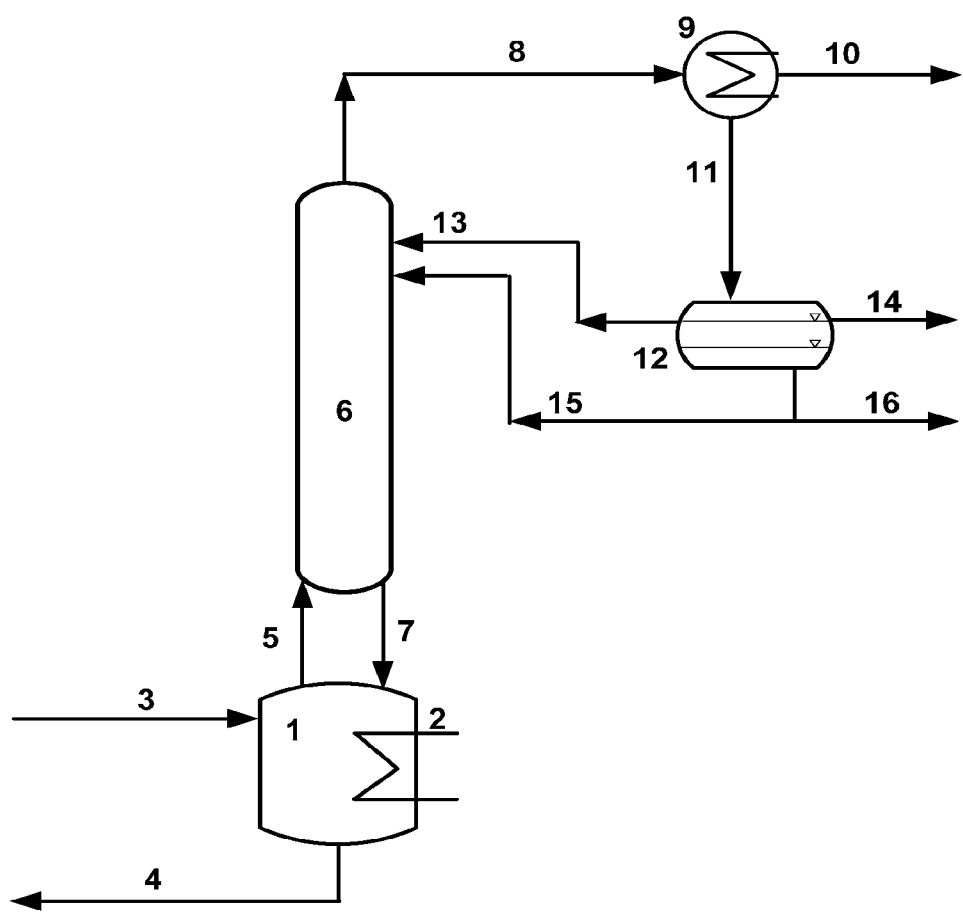
FIG. 1 shows a working example of the process of the invention up to the recovery of the mixture comprising the alkyl acrylate and the alcohol.

It has been recognized in accordance with the invention that the following advantages among others are achieved by the process of the invention:

Through the use of 3-hydroxypropionic acid, it is possible to prepare a virtually acetate-free butyl acrylate. 'Acetate' is understood here to mean n-butyl or isobutyl acetate [$H_3C—C(=O)—OR$].

In the conventional plants for preparation of acrylic acid (as an intermediate for the subsequent esterification), it is necessary to perform a complex removal of the acetic acid which likewise forms as well as the acrylic acid formed in the reaction, in order to avoid acetate formation in the subsequent esterification with the alcohol.

In addition, in a particular execution, an improved closed-loop control concept (see below) generates a higher yield of butyl acrylate again with lower energy consumption and another improvement in quality (especially purity).

Furthermore, in particular configurations, further-increased yields and/or product purities are achieved by means of a particular startup strategy (see below) and/or a particular stabilization concept (see below).

In a preferred process variant, the 3-hydroxypropionic acid used is biobased 3-hydroxypropionic acid.

"Biobased 3-hydroxypropionic acid" is understood to mean one that has been prepared proceeding from renewable raw materials.

It is further preferable that the biobased 3-hydroxypropionic acid has been prepared by fermentation, especially from glucose, xylose, arabinose, sucrose, fructose, cellulose, glucose oligomers and/or glycerol by fermentation, particularly with subsequent purification. For example, WO 2012/074818 A2 (Novozymes, Inc.) discloses the preparation of biobased 3-hydroxypropionic acid (abbreviation: bio-3-hydroxypropionic acid, shorter abbreviation: bio-HPS) from sugars such as glucose by fermentation and subsequent purification.

The aqueous bio-3-hydroxypropionic acid thus obtained comprises, for example, as well as water, essentially the following constituents:

35% to 70% by weight of 3-hydroxypropionic acid.
0% to 20% by weight of oligomeric 3-hydroxypropionic acid,
0% to 10% by weight of acrylic acid,
0% to 1% by weight of oligomeric acrylic acid
0.01% to 0.1% by weight of glycolic acid,
0.01% to 0.1% by weight of 2-hydroxypropionic acid,
0.005% to 0.05% by weight of formic acid,
0% to 0.15% by weight, particularly 0.0% to 0.05% by weight, for example
0.005% to 0.10% by weight, of acetic acid,
0.005% to 0.05% by weight of succinic acid, 0.005% to 0.05% by weight of fumaric acid,
0.0001% to 0.01% by weight of formaldehyde,
0.0001% to 0.01% by weight of acetaldehyde,
0.0001% to 0.01% by weight of methanol and
0.0001% to 0.01% by weight of ethanol.

Preferably, the molar use ratio of butanol R—OH to 3-hydroxypropionic acid is ≥1 and is further preferably below 5. A particularly advantageous molar use ratio of butanol R—OH to 3-hydroxypropionic acid is in the range from 1:1 to 3:1. A very particularly preferred molar use ratio is in the range from 1.1:1 to 1.8:1.

It is preferably a characteristic feature of the dehydrating and simultaneously esterifying conditions that a catalytically active amount of an acid is present. In an advantageous version of the invention, the content of catalytically active acid in the reactor, based on the reaction mixture present therein, is 0.1% to 20% by weight, particularly 5% to 15% by weight, further preferably 7% to 10% by weight. Preferred acids are mineral acids, such as sulfuric acid, phosphoric acid, and organic sulfonic acid. Among the organic sulfonic acids, preference is given to methanesulfonic acid, benzenesulfonic acid, dodecylbenzenesulfonic acid and/or p-toluenesulfonic acid. It is also possible to use a mixture of organic sulfonic acid(s) and mineral acid(s), for example sulfuric acid. It is particularly preferable to use sulfuric acid and/or organic sulfonic acid(s) as esterification and dehydration catalyst(s).

The reactants, i.e. the 3-hydroxypropionic acid and butanol R—OH reactants, are preferably converted in the reactor at a temperature in the range from 80 to 170° C., particularly in the range from 100 to 155° C., more particularly in the range from 120 to 140° C.

The residence time of the reactants, i.e. the 3-hydroxypropionic acid and butanol R—OH reactants, in the reactor is preferably 1 to 20, more preferably 2 to 8, hours. The residence time is understood to mean the time for which the bottoms draw volume (4) resides in the liquid volume of the reaction vessel (1).

In the simplest case, the rectification column (6) is placed directly atop the reaction vessel (1) (reaction vessel=reactor), and in general the vapors (5) ascending out of the reaction vessel are guided in countercurrent to the reflux volumes (13; 15) conducted into the rectification column.

Placing the column directly on top offers the advantage of conveying the vapors (5) formed in the reactor (1) directly without additional pipelines into the rectification column (6) and the liquid (7) effluxing from the column directly into the reactor (1). However, a separate arrangement of reaction vessel (1) and rectification column (6) is also possible, with corresponding pipelines for feeding of the vapors into the column and for efflux of the liquid flowing through the rectification column into the reaction vessel. Such an embodiment with an indirectly attached column is also encompassed by the expression 'reactor with rectification column'.

The rectification column (6) is of a design known per se and has the customary internals. Useful column internals are in principle all standard internals, for example trays, structured packings and/or random packings. Among the trays, preference is given to bubble-cap trays, sieve trays, valve trays, Thormann trays and/or dual-flow trays; among the random packings, preference is given to those comprising rings, helices, saddles, Raschig, Intos or Pall rings, Berl or Intalox saddles, or braids. Particular preference is given to dual-flow trays.

The efficacy of such internals within the rectification column should preferably correspond to at least five theoretical plates, for example in the range from 6 to 40 theoretical plates; more preferably, a separation performance of 10 to 30 theoretical plates should be provided.

In the process of the invention, the pressure at the top of the rectification column (6) is preferably in the range from 0.2 to 5.0 bar, particularly in the range from 0.3 to 3.0 bar, more particularly in the range from 0.5 to 1.2 bar.

Preferably, the separation into an aqueous phase and an organic phase is effected by means of a phase separator. In such an apparatus, two liquids that are not homogeneously miscible with one another can be separated by virtue of their difference in density. At least some of the aqueous phase obtained, which comprises not only water but also butanol R—OH, with or without traces of further components, is discharged. More preferably, 10% to 80% by weight, more particularly 20% to 70% by weight, of the aqueous phase obtained is discharged. The rest is recycled in each case, preferably into the rectification column (6).

Preferably, a portion of the organic phase obtained is likewise recycled, preferably into the rectification column. In particular, 0% to 80% by weight, e.g. 1% to 75% by weight, more particularly 5% to 50% by weight, of the organic phase is recycled, preferably into the rectification column. The other portion is discharged, and sent to a distillative separation.

The distillative separation of the organic phase discharged, comprising the butyl acrylate and the butanol (R—OH), is preferably effected in such a way that the butanol is removed overhead in a downstream rectification column (as described, for example, in EP 765 859 A1 (BASF AG)). Preferably, the butanol thus removed is recycled into the reactor (see below). Appropriately, the recycling is effected continuously, with or without intermediate vessels.

The resulting bottoms liquid from this rectification column consists essentially of the butyl acrylate and small amounts of high boilers and stabilizer used (for example what is called process stabilizer; for example especially phenothiazine (PTZ)).

In a further downstream rectification column, the butyl acrylate is typically removed overhead. In the condensation, preference is given to adding a stabilizer (called a storage stabilizer; for example MeHQ in particular). The bottoms liquid from this rectification column that comprises the higher-boiling by-products is appropriately preferably recycled into the reactor, preferably continuously, with or without intermediate vessels.

A particular embodiment (likewise described in EP 765 859 A1 (BASF AG)) involves withdrawing the butyl acrylate from the rectification column for recovery of butanol through a side draw after separation of any entrained liquid droplets, and condensing it to give the pure ester. In the condensation, a stabilizer (called the storage stabilizer; for example p-methoxyphenol (MeHQ) in particular) is added thereto. In this execution, the bottoms discharge from the butanol rectification column (consisting mainly of butyl acrylate) is preferably recycled into the reactor.

The butanol obtained after the separation is particularly advantageously recycled at least partly to the conversion in the reactor. Preference is given to recycling 5% to 100% by weight, more preferably 80% to 100% by weight, of the alcohol.

The process of the invention is more preferably used for preparation of n-butyl acrylate, wherein aqueous, particularly biobased, 3-hydroxypropionic acid is converted in the presence of the alcohol n-butanol.

By the process of the invention, it is possible to prepare n-butyl acrylate with, in particular, a purity of ≥99.0% by weight, more particularly ≥99.5% by weight, and an n-butyl acetate content of ≤1000 ppm, more particularly of ≤100 ppm. In particular, the acrylic acid content is <100 ppm, e.g. 5 to 80 ppm.

By the process of the invention, it is possible to prepare isobutyl acrylate with, in particular, a purity of ≥99.0% by weight, more particularly ≥99.5% by weight, and an isobutyl acetate content of ≤1000 ppm, more particularly of ≤100 ppm. In particular, the acrylic acid content is <100 ppm, e.g. 5 to 80 ppm.

In the process of the invention, the butyl acrylate formed is preferably stabilized by suitable polymerization inhibitors in order to avoid unwanted polymerization. In other words, the process of the invention is preferably conducted in the presence of effective amounts of one stabilizer or a plurality of stabilizers. Suitable stabilizers are in principle all polymerization inhibitors that are recommended for stabilization of acrylic acid and acrylic esters in, for example, DE 10 2005 053 982 A1 (BASF AG) and DE 102 58 329 A1 (BASF AG).

Suitable stabilizers may, for example, be N-oxides (nitroxyl or N-oxyl radicals, i.e. compounds having at least one >N—O group), for example 4-hydroxy-2,2,6,6-tetramethylpiperidine N-oxyl (4HT) or 4-oxo-2,2,6,6-tetramethylpiperidine N-oxyl, phenols and naphthols, such as p-methoxyphenol, p-aminophenol, p-nitrosophenol, 2-tert-butylphenol, 4-tert-butylphenol, 2,4-di-tert-butylphenol, 2-methyl-4-tert-butylphenol, 2,6-tert-butyl-4-methylphenol or 4-tert-butyl-2,6-dimethylphenol, quinones, for example hydroquinone or hydroquinone monomethyl ether, aromatic amines, for example N,N-diphenylamine, phenylenediamines, for example N,N'-dialkyl-p-phenylenediamine, where the alkyl radicals may be the same or different and each independently have 1 to 4 carbon atoms and may be straight-chain or branched, for example N,N'-dimethyl-p-phenylenediamine or N,N'-diethyl-p-phenylenediamine, hydroxylamines, for example N,N-diethylhydroxylamine, imines, for example methyl ethyl imine or methylene violet, sulfonamides, for example N-methyl-4-toluenesulfonamide or N-tert-butyl-4-toluenesulfonamide, oximes, such as aldoximes, ketoximes or amide oximes, for example diethyl ketoxime, methyl ethyl ketoxime or salicylaldoxime, phosphorus compounds, for example triphenylphosphine, triphenyl phosphite or triethyl phosphite, sulfur compounds, for example diphenyl sulfide or phenothiazine, metal salts, for example cerium(III) acetate or cerium(III) ethylhexanoate, but also various copper salts, for instance Cu(II) dialkyldithiocarbamates, for example Cu(II) dibutyldithiocarbamate, and also Cu(II) oxinate (oxine=4-hydroxyquinoline), and additionally manganese salts, for example Mn(II) diacetate or mixtures thereof.

Stabilization is preferably effected with phenothiazine (PTZ), p-methoxyphenol (MeHQ), hydroquinone, hydroquinone monomethyl ether, 4-hydroxy-2,2,6,6-tetramethylpiperidine N-oxyl, 4-oxo-2,2,6,6-tetramethylpiperidine N-oxyl, 2,6-tert-butyl-4-methylphenol or mixtures thereof.

Very particular preference is given to using phenothiazine (PTZ) and/or p-methoxyphenol (MeHQ) and/or 4-hydroxy-2,2,6,6-tetramethylpiperidine N-oxyl (4HT) as polymerization inhibitor.

Even when the inhibitors can be added as a pure substance, it is advantageous to add the inhibitor dissolved in a solvent as a solution that can be dosed in a simple and reproducible manner, although inhibitor mixtures in a single solution are also possible in principle. Preference is given to using a liquid already present in the acrylate synthesis process or the substance mixture in the column as solvent. Particularly preferred for choice as solvent is the acrylate product (i.e. the butyl acrylate) itself, water or one of the synthesis feedstocks for the acrylate (e.g. the butanol R—OH).

The process of the invention is advantageously conducted with particular measures for control of certain parameters. This process control is preferably effected as follows:

For the production of on-spec butyl acrylate, i.e. a product having high purity, the separation of acrylic acid from the butyl acrylate in the rectification column (6) is of crucial importance.

It has been found here to be advantageous to set a defined ratio between the organic reflux (13) and the aqueous reflux (15). This reflux ratio of streams 13 to 15 is preferably in the range of 0.1-1.0.

In addition, the reaction volume in the bottom (1) of the column (or independent reaction vessel in the case of an indirectly attached column), which is crucial for the conversion, is preferably kept constant or virtually constant (+/−10% by volume). This can be achieved firstly by discharging a constant or virtually constant (+/−10% by volume) liquid stream (4) from the reaction volume (1) with a constant or virtually constant (+/−10% by volume) liquid level in the reaction vessel. In addition, the bottoms draw volume (4) should preferably be in a particular ratio to the feed (3), preferably in a ratio of streams 4 to 3 in the range of 0.01-0.30.

A second measure is a quality control with regard to the acrylic acid content in the organic distillate (14). Since the liquid volume in the reaction space (1) reacts strongly to the aqueous reflux volume (15), the liquid level in the reactor (1) is preferably under closed-loop control via the reflux volume (=recycled volume) of the aqueous phase (15). The aqueous reflux ensures that the high boilers n- or isobutyl acrylate and the corresponding butanol (R—OH) can be distilled off owing to the formation of a low-boiling azeotrope.

The organic reflux ensures that the concentration of the acrylic acid formed in the reactor (1) remains below the concentration of, in particular, 100 ppm.

Through the control of the amount of the organic reflux (13), it is possible to combine several effects: purifying by distillation, increasing the residence time in the reaction space, increasing the concentration of butanol (R—OH) in the reaction space (1).

This closed-loop control strategy leads to particularly stable operation in the reaction vessel (1) and in the rectification column (6).

In a preferred embodiment (cf. FIG. 2), in the process of the invention, at least one stabilizer (stabilizer 1) is present in the rectification column (6), which dissolves in effective proportions both in the aqueous phase and in the organic phase. In particular, such a stabilizer, such as 4HT in particular, is added (17) above the uppermost theoretical plate of the column (6). This results in stabilization of the entire rectification column (6) with the stabilizer.

In addition (cf. FIG. 2), in the process of the invention, preference is given to adding at least one stabilizer that dissolves in effective proportions both in the aqueous phase and in the organic phase to the phase separator (12) that collects the condensate (11), (18), and/or to the conduit of a quench circuit (19) and/or at the top of the condenser (9). This stabilizer is preferably identical to stabilizer 1 (especially 4HT). The quench circuit that is preferably set up (i.e. the liquid recycle stream of a portion of the condensate, e.g. 10 to 50 hundredths of the condensate by weight, into the condenser (9)) has the function that the vapors (8) that are naturally free of stabilizer are stabilized particularly adequately on condensation in the condenser (9). Effective amounts of stabilizer present in solution in the respective phase are, overall, particularly 10 ppm by weight, for example in the range from 10 to 1000 ppm by weight. If a stabilizer used in this respect does not dissolve completely in the respective liquid phase, it is correspondingly present in suspended form. In the presence of a stabilizer as a suspension in the liquid phase(s), this particulate stabilizer component which is barely effective or ineffective a priori can offer advantages by virtue of its effect as a stabilizer depot since, for example in the case of the chemical degradation of dissolved stabilizer, which worsens its efficacy, further stabilizer which is then freshly active additionally goes into solution from the suspended component, which can even occur across phase boundaries in the case of suitably intimate contact between liquid phases and can be influenced via the size distribution of the particles. The stabilizers can each be used, more particularly, as a solution in a suitable solvent, particularly as detailed above, for example the alcohol used in the process, water, the corresponding butyl acrylate, for example in each case as a 1-5% by weight solution (for example via conduits 17/18, FIG. 2).

Advantageously, a stabilizer 2 (20), especially PTZ, which is suitable for higher temperatures, and a stabilizer 3 (20) (especially MeHQ), which also stabilizes the transition region between reaction space and the lower part of the column owing to its higher vapor pressure, are added to the reaction vessel (1).

Figure 2:
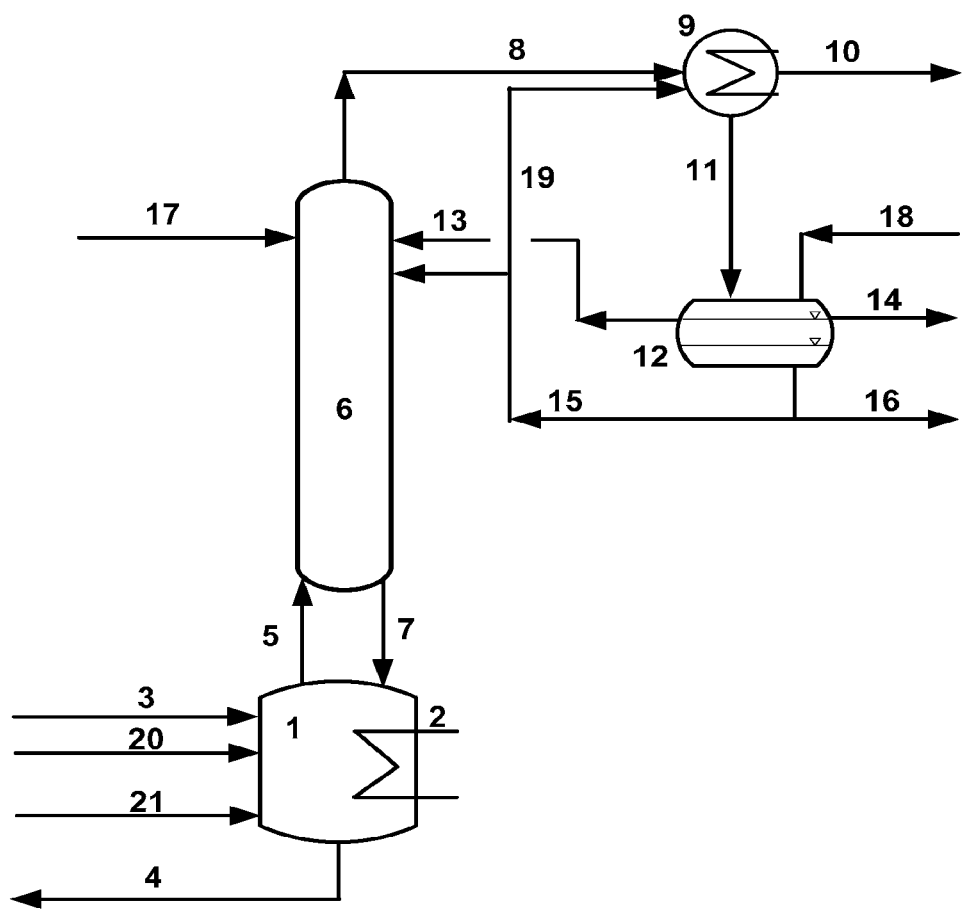
FIG. 2 shows a preferred embodiment of the process of the invention. At least one stabilizer (stabilizer 1) is present in the rectification column (6), which dissolves in effective proportions both in the aqueous phase and in the organic phase. In particular, such a stabilizer, such as 4HT in particular, is added (17) above the uppermost theoretical plate of the column (6). This results in stabilization of the entire rectification column (6) with the stabilizer.

The stabilizers 2 and 3 may each be used, more particularly, as a solution in a suitable solvent, particularly as detailed above, for example the butyl acrylate formed correspondingly in the process or in the 3HPA or butanol (R—OH) reactants used (for example via conduit 20, FIG. 2).

Advantageously, in the process of the invention, an oxygenous gas is additionally used to inhibit polymerization. Particularly suitable for this purpose are air/nitrogen mixtures, for example with an oxygen content of 4% to 9% by volume.

If an oxygenous gas is used to inhibit polymerization, it is preferably fed in at the lower end of the evaporator (2) or at the lower end of the reaction space (1) (cf. 21 in FIG. 2).

The startup of the process of the invention comprising the conversion in the reaction vessel (1) and the distillation in the column (6) can be afflicted with problems, since, in particular, changes in the reflux volumes of the two streams 13 and 15 can have significantly different effects on the overall system.

Changes in the volume of the aqueous reflux (15) affect the steam volume formed relatively rapidly, and changes in the volume of the organic reflux (13) affect the acrylic acid concentration in the top of the column relatively slowly. But the two reflux volumes are not independent of one another. The following has been recognized in accordance with the invention: if the exact reflux volumes are not well-matched to one another, the evaporation can stop, or the column (6) floods owing to an excessively high volume of steam. It is then very difficult to get the system back into the normal operating state.

Advantageously, therefore, for startup, the vessel 1 (the reactor) is first charged with an appropriate amount of a corresponding reaction mixture comprising the butyl acrylate, especially bottom product from a prior production campaign, or the corresponding butyl acrylate. Then the bottoms are heated to operating temperature (conversion temperature) and the feeds of 3HPA, butanol and catalyst are put into operation.

All pressure figures are based on absolute pressure.
All ppm figures are based on weight.

EXAMPLES

Example 1a

FIG. 1 shows a working example of the process of the invention up to the recovery of the mixture comprising the alkyl acrylate and the alcohol.

FIG. 1 shows a reaction vessel 1 (=reactor), a rectification column 6 having separating internals. Via a feed conduit 3, a mixture of aqueous 3-hydroxypropionic acid (3HPA) and butanol (R—OH), and also p-toluenesulfonic acid as esterification catalyst is fed in. The gaseous reaction product is fed from the top of the reactor 1 via a conduit 5 to a rectification column 6. The conduit 4 provided in the lower portion of the reactor 1 serves for disposal of remaining residues.

The vapor mixture that flows continuously out of the reaction zone into the rectification column 6 is rectified therein, and the aqueous azeotrope comprising the target ester to be formed, flowing away from the top of this rectification column 6 via conduit 8, and consisting predominantly of acrylate, alcohol and water, is fed to a condenser 9 optionally supplemented by an aftercooler, and partly condensed therein. The uncondensed component from the condenser 9 comprises the lower-boiling impurities and is drawn off in vaporous form as stream 10.

The condensate flows via a conduit 11 into a liquid/liquid phase separator 12. The azeotrope separates therein into an aqueous phase and an organic phase. The aqueous phase consisting mainly of water and some alcohol and acrylate is partly fed via conduit 15 to the top of rectification column 6 in order to bring about the rectificative separation and the azeotrope formation of the vapors that ascend therein. A further portion is withdrawn via conduit 16 for stripping-off of alcohol. Organic reflux from the separator 12 is introduced via conduit 13 into the top of the rectification column 6 in order to send the acrylic acid back.

At the lower end of the column, the liquid 7 is partly evaporated in an evaporator 2 and recycled into the column via the pipeline 5. A substream 4 comprising the higher-boiling impurities is drawn off. The evaporator 2 may take the form of a heatable vessel, of a natural circulation evaporator or of a forced circulation evaporator; in the latter case, a circulation pump for the liquid stream 4 is additionally required. With regard to the avoidance of unwanted polymerization reactions, it is particularly advantageous to use a forced circulation/flash evaporator since no evaporation at the heated surfaces takes place with this design.

Example 1b

The mode of operation is represented using the data from a thermodynamic simulation of an overall plant for preparation of butyl acrylate.

The thermodynamic simulation of the process was conducted with the Aspen Plus® software (Aspen for short). Aspen is an extensive piece of simulation software which is used for modeling, simulation and optimization of chemical processes and plants in the industry. Aspen has access to numerous model databases for modeling the basic operations and to substance databases for the physical properties of many different substances. The properties of mixtures are calculated by Aspen with the aid of different thermodynamic models from the physical data of the pure substances.

The thermodynamic simulation of the overall plant led to the following results:

The following mixture is fed to the reactor 1 via a feed conduit 3:
aqueous 3-hydroxypropionic acid (3HPA): 1000 g/h
n-butanol: 953 g/h
p-toluenesulfonic acid: 4 g/h The following mixture is fed to the reactor 1 via a feed conduit 20:
n-butanol: 9.8 g/h
MeHQ: 0.1 g/h
PTZ: 0.1 g/h An oxygenous gas is fed to the reactor 1 via a feed conduit 21:
nitrogen: 9.5 L/h
oxygen: 0.5 L/h The aqueous 3-hydroxypropionic acid has the following composition:
water: 20% by weight
3-hydroxypropionic acid: 80% by weight
acetic acid: <0.01% by weight The following mixture is fed to the phase separator 12 via a feed conduit 18:
water: 9.9 g/h
4HT: 0.1 g/h The conversion is conducted at a temperature of 150° C., a pressure of 1 bar and a residence time of 2 h.

217 g/h of the organic phase from the liquid/liquid phase separator 12 are returned as reflux via conduit 13 to column 6, and 1444 g/h are drawn off via conduit 14 as organic distillate.

The organic phase has the following composition:
water: 7% by weight
n-butanol: 23% by weight
n-butyl acrylate: 70% by weight
acrylic acid: <0.01% by weight
n-butyl acetate: <0.01% by weight
4HT: <0.01% by weight 425 g/h of the aqueous phase from the liquid/liquid phase separator 12 are returned as reflux via conduit 15 to column 6, and 425 g/h are drawn off via conduit 16 as aqueous distillate.

The aqueous phase has the following composition:
water: 95% by weight
n-butanol: 3% by weight
n-butyl acrylate: 2% by weight
acrylic acid: <0.01% by weight
n-butyl acetate: <0.01% by weight
4HT: <0.01% by weight In the lower part of the reactor, 108 g/h are drawn off as liquid residue via conduit 4.

The residue has the following composition:
water: 1% by weight
n-butanol: 3% by weight
n-butyl acrylate: 16% by weight
acrylic acid: 3% by weight
n-butyl acetate: <0.01% by weight
high boilers: 77% by weight
MeHQ: <0.1% by weight
PTZ: <0.1% by weight
4HT: <0.01% by weight The organic phase can then be worked up by the known process steps (especially according to EP 765 859 A1 (BASF AG), cf. top of page 8) to give the pure n-butyl acrylate product.

The pure product has the following composition:
water: <0.01% by weight
n-butanol: <0.01% by weight
n-butyl acrylate: >99.5% by weight
acrylic acid: <0.01% by weight
n-butyl acetate: <0.01% by weight The example demonstrates the advantageous properties by way of example with regard to the low n-butyl acetate content in the pure product.

The invention claimed is:

1. A process for continuously preparing a butyl acrylate $H_2C=CH-C(=O)OR$, wherein R is n-butyl or isobutyl, the process comprising:
    converting aqueous 3-hydroxypropionic acid under dehydrating and esterifying conditions in the presence of a corresponding butanol R—OH in a reactor comprising a rectification column and distilling off a ternary azeotrope comprising butyl acrylate, unconverted butanol and water as an overhead from the rectification column, separating the overhead into a liquid aqueous phase and a liquid organic phase comprising the butyl acrylate and the butanol, at least partially discharging each of the aqueous and organic phases after the separation, and
    separating by distillation the organic phase comprising the butyl acrylate and the butanol.

2. The process according to claim 1, wherein the aqueous 3-hydroxypropionic acid is a biobased 3-hydroxypropionic acid.

3. The process according to claim 2, wherein the biobased 3-hydroxypropionic acid is prepared by fermentation.

4. The process according to claim 1, wherein a molar ratio of butanol R—OH to 3-hydroxypropionic acid is at least 1.

5. The process according to claim 1, wherein the dehydrating and esterifying conditions comprise a catalytically active amount of an acid in the reactor.

6. The process according to claim 5, wherein the acid is sulfuric acid, an organic sulfonic acid or a combination thereof.

7. The process according to claim 1, wherein the converting in the reactor proceeds at a temperature of from 80 to 170° C.

8. The process according to claim 1, wherein a residence time of reactants in the reactor is from 1 to 20 hours.

9. The process according to claim 1, wherein the rectification column has at least 5 theoretical plates.

10. The process according to claim 1, wherein a pressure at the top of the rectification column is from 0.2 to 5.0 bar (absolute).

11. The process according to claim 1, wherein the separating by distillation comprises distilling off the butanol in a rectification column and producing a bottom liquid comprising the butyl acrylate and then distilling out the bottom liquid in an additional rectification column to obtain butyl acrylate.

12. The process according to claim 1, wherein the butanol obtained after the separating by distillation is at least partly recycled to the converting in the reactor.

13. The process according to claim 1, wherein the converting comprises converting the aqueous 3-hydroxypropionic acid in the presence of n-butanol.

14. The process according to claim 1, wherein the converting comprises converting the aqueous 3-hydroxypropionic acid in the presence of isobutanol.

15. The process according to claim 13, wherein the n-butyl acrylate has a purity of at least 99.0% by weight and a n-butyl acetate content of 1000 ppm or less by weight.

16. The process according to claim 14, wherein the isobutyl acrylate has a purity of at least 99.0% by weight and an isobutyl acetate content of 1000 ppm or less by weight.

17. The process according to claim 1, wherein the converting is conducted in the presence of an effective amount of at least one stabilizer.

18. The process according to claim 1, further comprising refluxing back to the reactor at least a portion of the aqueous phase, wherein a liquid level in the reactor is under closed-loop control via a reflux volume of the aqueous phase.

19. The process according to claim 1, further comprising initially charging the reactor with the corresponding butyl acrylate or a corresponding reaction mixture comprising the butyl acrylate to start the process.

\* \* \* \* \*